(12) United States Patent
Breaux et al.

(10) Patent No.: US 12,161,482 B2
(45) Date of Patent: Dec. 10, 2024

(54) SYSTEM, DEVICE, AND METHODS FOR HYDRATION MONITORING

(71) Applicant: HAPPY HEALTH INC., Austin, TX (US)

(72) Inventors: James Breaux, Austin, TX (US); Dustin M. Freckleton, Austin, TX (US); Nithin O. Rajan, Austin, TX (US); Byron P. Olson, Boone, IA (US); David E. Clift-Reaves, Austin, TX (US); Paulo E. Xavier Da Silveria, Boulder, CO (US); Namita D. Lokare, Austin, TX (US)

(73) Assignee: Happy Health, Inc., Austin, TX (US)

(*) Notice: Subject to any disclaimer, the term of this patent is extended or adjusted under 35 U.S.C. 154(b) by 0 days.

(21) Appl. No.: 17/492,780

(22) Filed: Oct. 4, 2021

(65) Prior Publication Data
US 2022/0022812 A1 Jan. 27, 2022

Related U.S. Application Data

(63) Continuation of application No. 16/158,157, filed on Oct. 11, 2018, now Pat. No. 11,134,891.

(51) Int. Cl.
*A61B 5/01* (2006.01)
*A61B 5/00* (2006.01)
(Continued)

(52) U.S. Cl.
CPC .............. *A61B 5/4875* (2013.01); *A61B 5/01* (2013.01); *A61B 5/02055* (2013.01); *A61B 5/02108* (2013.01); *A61B 5/024* (2013.01); *A61B 5/02405* (2013.01); *A61B 5/026* (2013.01); *A61B 5/0261* (2013.01); *A61B 5/0537* (2013.01); *A61B 5/0816* (2013.01); *A61B 5/14551* (2013.01); *A61B 5/1495* (2013.01); *A61B 5/318* (2021.01); *A61B 5/4842* (2013.01);
(Continued)

(58) Field of Classification Search
CPC .... A61B 2560/0247; A61B 2562/0219; A61B 2562/029; A61B 5/01; A61B 5/02055; A61B 5/02108; A61B 5/024; A61B 5/02405; A61B 5/026; A61B 5/0261; A61B 5/0537; A61B 5/0816; A61B 5/14551; A61B 5/1495; A61B 5/318; A61B 5/443; A61B 5/4842; A61B 5/4875; A61B 5/6802; A61B 5/72; A61B 5/7225; A61B 5/7264; G16H 50/20
See application file for complete search history.

(56) References Cited

U.S. PATENT DOCUMENTS

2015/0305675 A1* 10/2015 Miller .................... G16H 40/67
600/301
2016/0235374 A1* 8/2016 Miller .................. A61B 5/7275
(Continued)

*Primary Examiner* — Amanda K Hulbert
(74) *Attorney, Agent, or Firm* — Polsinelli PC

(57) ABSTRACT

A method of monitoring hydration including obtaining biological data for a given period of time, wherein the biological data includes measurements of one or more biological indicators; converting the biological data into a baseline value; obtaining real-time biological data from one or more biological sensors; performing a pre-processing analysis of the real-time biological data; comparing the real-time biological data with baseline value to create a hydration index.

6 Claims, 12 Drawing Sheets

(51) Int. Cl.
*A61B 5/0205* (2006.01)
*A61B 5/021* (2006.01)
*A61B 5/024* (2006.01)
*A61B 5/026* (2006.01)
*A61B 5/0537* (2021.01)
*A61B 5/08* (2006.01)
*A61B 5/1455* (2006.01)
*A61B 5/1495* (2006.01)
*A61B 5/318* (2021.01)

(52) U.S. Cl.
CPC .......... *A61B 5/6802* (2013.01); *A61B 5/7225* (2013.01); *A61B 5/7264* (2013.01); *A61B 5/443* (2013.01); *A61B 5/72* (2013.01); *A61B 2560/0247* (2013.01); *A61B 2562/029* (2013.01)

(56) References Cited

U.S. PATENT DOCUMENTS

2016/0310023 A1 10/2016 Chachisvilis et al.
2017/0049352 A1 2/2017 Mirov

* cited by examiner

SYSTEM, DEVICE, AND METHODS FOR HYDRATION MONITORING

CROSS-REFERENCE TO RELATED APPLICATION(S)

This application is a continuation of U.S. patent application Ser. No. 16/158,157, filed Oct. 11, 2018, which claims priority to U.S. Provisional Application No. 62/570,966, filed Oct. 11, 2017, each application being fully incorporated by reference herein.

TECHNICAL FIELD

The present technology pertains to a wearable system, a device, and a series of methods capable of monitoring a hydration level of a user. In particular, the present disclosure relates to a system and method for monitoring one or more biological indicators to create a baseline hydration state which can be used to determine a hydration index at a later point in time.

BACKGROUND

Hydration level is an important component to every aspect of health, even small deviations from proper hydration levels, or a euhydrated state, can have drastic consequences. For example, going through periods of severe dehydration can cause a variety of medical issues which can lead to increased health care expenses.

Typical methods of tracking hydration, or dehydration, levels included monitoring thirst drive, urine color, urine analysis, and performing a sweat test. While these methods are able to track specific water compartments, such methods can be inaccurate, fail to provide a holistic hydration measurement, and are not able to provide a real-time analysis of hydration level. For example, the monitoring or urine color and urine osmolality can allow an individual to track urine accumulated since the last urination, it fails to track several other factors including plasma osmolality and change in nude body weight. In another example, tracking only sweat analyses only allows individuals a partial view of their hydration, since sweat analysis cannot be performed when an individual is involved in sedentary activities. Additionally, such methods don't take into account various biological, environmental, or demographic data which can significantly affect how hydration affects an individual.

Numerous monitoring devices have been developed to track various aspects of a user's health. Such devices can be capable of tracking one or more factors such as a user's heart rate, activity throughout a defined period, steps throughout a defined period, wellness, and the like. Such devices can be wearable and in some examples can be integrated into garments, hats, wrist bands, watches, socks, shoes, eyeglasses, headphones, smartphones, and any other wearable item. Such devices can be configured to perform health and wellness tracking.

BRIEF DESCRIPTION OF THE DRAWINGS

A description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
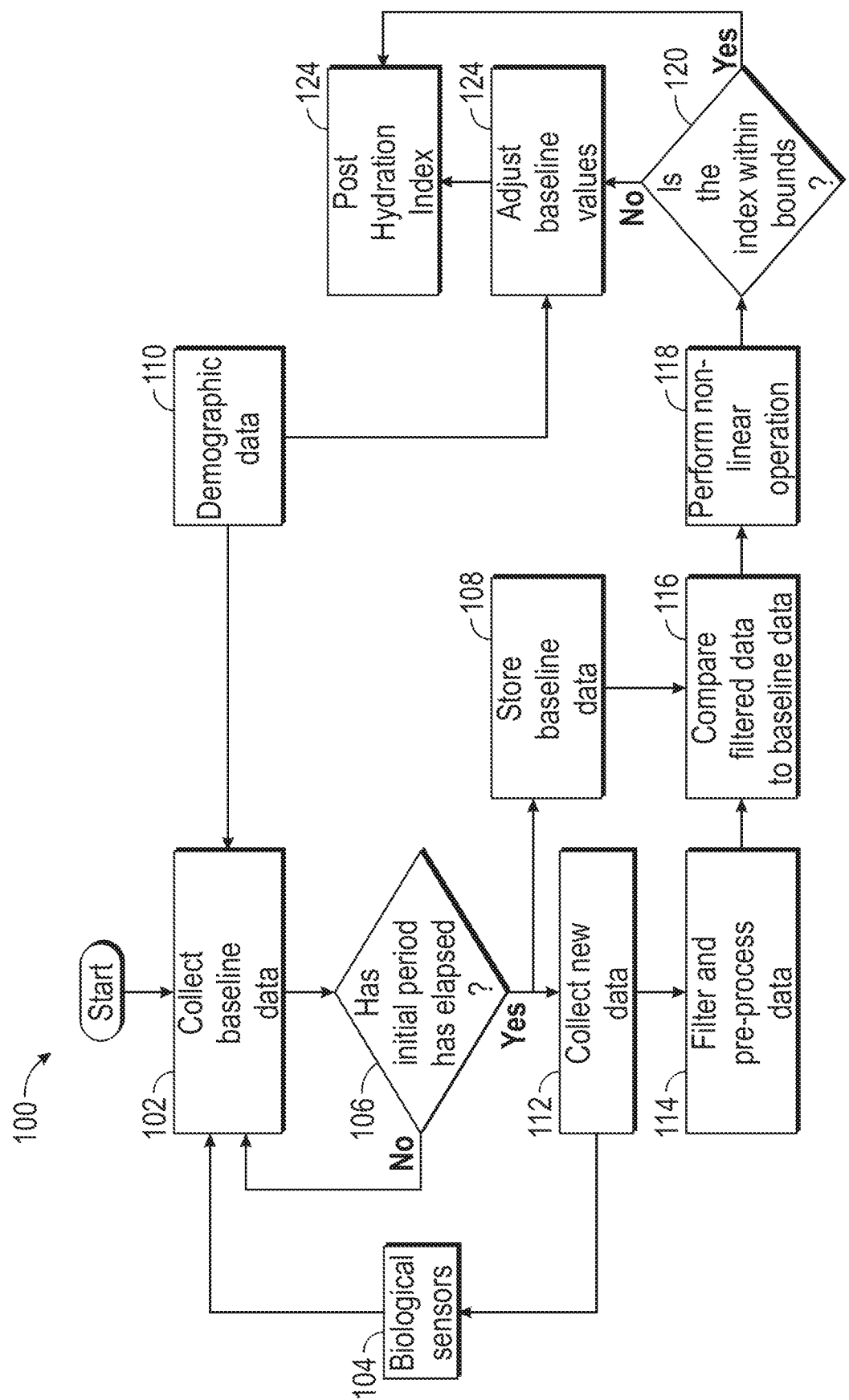
FIG. 1 is a flow chart of an exemplary hydration monitoring method in accordance with the disclosure herein.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Numerous specific details are set forth in the present disclosure in order to provide a thorough understanding of the embodiments described herein. However, it will be understood by those of ordinary skill in the art that the embodiments described herein can be practiced without these specific details. In other instances, methods, systems, and devices have not been described in detail so as not to obscure the related relevant feature being described. The description is not to be considered as limiting the scope of the embodiments described herein.

Several definitions that apply throughout this disclosure will now be presented. The term "coupled" is defined as connected, whether directly or indirectly through intervening components, and is not necessarily limited to physical connections. The term "substantially" is defined to be essentially conforming to the particular dimension, shape or other word that substantially modifies, such that the component need not be exact. The terms "comprising," "including" and "having" are used interchangeably in this disclosure. The terms "comprising," "including" and "having" mean to include, but not necessarily be limited to the things so described.

As used herein, the term "euhydrated state" refers to a normal level of hydration, absent substantial hyper-hydration or dehydration.

As used herein, the term "hydration index" refers to a hydration, or dehydration, level indicator based on the deviation of biological indicators as compared to their baseline levels during euhydration.

As used herein, the term "biomonitoring sensor" refers to any device that can measure and report information regarding one or more biological indicators.

The present disclosure is drawn to a wearable system and method for monitoring the hydration level of a user. The system includes one or more biomonitoring sensors, operable to determine a baseline euhydrated state of the user, and monitor/detect deviations from said baseline. The system can be operable to provide the user with a measurement, such as a hydration index, indicating the deviation from a baseline hydration level of the user. Specifically, the wearable device and methods described in the present disclosure can benefit first-responders, clinicians, military personnel, athletes, as well as everyday users, by providing a better hydration measurement than thirst drive alone. One aspect of the present disclosure is to provide users with real-time access to a metric describing their current hydration state, such that the user can readily implement strategies to maintain optimal hydration throughout changing circumstances.

Even though water is one of the key constituents of the human body (40%-70% of total body weight) and an important component to every aspect of health, there currently is no effective method to continuously monitor hydration (Skelton, H. "The storage of water by various tissues of the body," *Arch. Int. Med., Vol.* 40, pp. 140-152 (1927)). This is despite the fact that even small deviations from proper hydration levels (the euhydrated state) can have drastic consequences and result in billions of dollars in healthcare expenditures each year.

It is generally recommended that adults need to drink about 3.2 L of water each day (3.7 L/day for men and 2.7 L/day for women) to maintain good health. (Popkin, Barry M., Kristen E. D'Anci, and Irwin H. Rosenberg. "Water, Hydration and Health." *Nutrition reviews,* Vol. 68, No. 8 (2010): 439-458. PMC. Web. 3 Nov. 2016). This general recommendation, however, needs to be significantly modified based on many user demographic factors including: age, sex, height, weight, body composition, temperature and humidity, activity level, diet, sweat rate, and direct access to fluids. With such a large number of factors to consider, it is no surprise that chronic dehydration remains such a prevalent problem.

Various aspects of an individuals' daily life can have significant changes on their hydration level, such aspects can include those of which a person may not be aware. Clinical dehydration is defined by losses in body water volume by as little as 1%-2% of total body weight and can be the result of both acute and chronic conditions. Chronic dehydration, in particular, is a widespread problem affecting people of every age, gender, race, and socioeconomic background. It is estimated that 75% of the Western adult population suffers from chronic dehydration, increasing to 90% in elderly populations, and to 84% in children (Fadda, R. et al "Effects of drinking supplementary water at school on cognitive performance in children," *Appetite,* Vol. 59, no. 3 (2012)). Moreover, scientific and experimental evidence confirms the difficulty of guessing proper hydration in individuals using external visual cues (Steiner, M. J. et al "Is this child dehydrated?" JAMA, vol. 291, no. 22 (2004)), and the challenges associated with determining hydration state even when using invasive methods (Armstrong, L. E. "Assessing Hydration Status: The Elusive Gold Standard," *Journal of the American College of Nutrition,* Vol. 26, No. 5, pp. 575S-584S (2007)). This is exacerbated by the fact that the thirst drive is known to be insufficient and has evolved as more of a protective mechanism rather than a drive to maintain optimal hydration status (Zimmerman, C. A. et al "Thirst neurons anticipate the homeostatic consequences of eating and drinking" *Nature,* Vol. 537, pp. 680-684 (2016)).

The human body requires proper hydration in order to maintain peak function. Systems and methods capable of accurately and effectively detecting hydration state of the human body, and differentiating it from the natural thirst drive, can improve the overall health of a subject. In trials performed using the disclosed system and methods, experimental data acquired in multiple subjects involving more than 1100 trials and more than 700 hours of monitoring has demonstrated that this goal can be accomplished using non-invasive sensors, similar to those found in wearable sensors available today, combined with specialized hydration-monitoring algorithms.

The human body strives to maintain homeostasis in order to maintain proper health and functioning. While doing so, biological signals or indicators which are indirectly associated with the imbalanced factor tend also to deviate from nominal baseline values. Such deviations can be used as indirect metrics of imbalances, and that is especially valuable when the indirect signals are easier (such as, more reliable, more accurate, more robust) to monitor than the imbalanced factors.

For example, while becoming dehydrated the human body will absorb fluid from blood plasma through osmosis in order to maintain proper extracellular and intracellular fluid flow and allow the continuation of intracellular biochemical reactions.

Maintaining blood flow is critical to sustain proper tissue perfusion. Thus, as plasma volume is reduced, tissue perfusion is maintained by increasing the resting heart rate in order to maintain cardiac output. That is to say, the same homeostasis that makes it more difficult to detect changes of hydration state directly in tissue also makes it easier to detect the resulting increase in the resting heart rate (RHR) of the individual. In an additional example, when an individual is dehydrated his/her breaths tend to become shallower and tend to repeat at a faster rate. Other examples of signals that deviate from baseline as a function of the user hydration status are tissue oxygenation, arterial oxygenation, localized hemoglobin concentration, total hemoglobin concentration, localized skin temperature and the interval between heart beats. Table 1, provided below, indicates how the baseline level of each one of these parameters can be affected by increasing levels of dehydration in a given user population.

TABLE 1

| Parameter | Symbol | Baseline change due to increasing dehydration |
|---|---|---|
| Resting heart rate | RHR | Increase |
| Tissue oxygenation | SmO2 | Decrease |
| Arterial oxygenation | SpO2 | Decrease |
| Skin perfusion | stHb | Decrease |
| Total hemoglobin concentration | tHb | Increase |
| Interval between heart beats | RR | Decrease |
| Tissue water absorption | $\alpha_t$ | Decrease |
| Skin temperature | $T_{skin}$ | Increase |
| Core temperature | $T_{core}$ | Decrease |
| NIRS Fractional water | pH2O | Decrease |
| Interval between breaths | IBB | Decrease |
| Depth of breath | DB | Decrease |

The biological parameter trends shown in Table 1 are generic and, under certain circumstances, one or more of the biological parameters can be anti-trending, or trend in the opposite direction, depending on the physiological condition of the particular individual. For example, while the generic trending behaviors described above relate to a large portion of the general population, individuals spanning a wide range of demographic factors, including, but not limited to, age, gender, body mass index, skin area, tissue fat percentage, Fitpatrick skin type, and the like, can cause a variation in the standard trends. Then, the deviation from baseline of any single parameter or a combination of parameters can be used to determine the user's deviation from their euhydrated (baseline) state.

A hydration index can be determined by taking the above factors into consideration. Specifically, a hydration index (or dehydration level) is determined by evaluating the deviation of one or more biological indicators as compared to a baseline level of an individual determined during euhydration. FIG. 1 illustrates an exemplary flowchart describing one method 100 which can be used to measure a hydration index of a user. In at least one example, the method 100 can include collecting the baseline data 102. The baseline data can include information regarding one or more biological indicators of an individual over a period of time. The biological indicators can include, but are not limited to, the biological parameters listed in Table 1. In at least one example, the collection of baseline data 102 can include an initial measurement period of, for example, 24 hours, during which the method receives biological indicator data from one or more biological sensors 104. In certain examples, the initialization period can be dependent on the needs of the individual or the amount of time available. For instance, in at least one example, the time frame for determining baseline data can be as low as about 1 second, or about 10 minutes. In an alternative example, the time used to determine baseline data can be about 1 week.

Biological sensors 104 compatible with the disclosed wearable device and methods can include at least one of heart rate monitors, arterial blood saturation (SpO$_2$) monitors, near infrared spectrometers (NIRS), electrocardiogram (EKG) monitors, tissue oxygenation monitors and any other monitors capable of monitoring and recording biological parameters. The biological indicators described herein can include one or more of heart rates (HR), inter-beat interval (or "RR" heart rate intervals), arterial blood saturation (SpO$_2$), tissue oxygenation (StO$_2$), muscle saturation (SmO$_2$), venous saturation (SvO$_2$), skin perfusion (stHb), total hemoglobin concentration (tHb), resting heart rate (RHR), skin temperature (T$_{skin}$), core temperature (T$_{core}$), interval between breaths, depth of breath, and fractional water, which can be measured by a differential NIRS sensor (as described in PCT/US2016/034411, which is incorporated by reference herein in its entirety). Additional biological indicators, not included in Table 1, which can vary in response to hydration level can include, but are not limited to, heart rate variability (HRV), blood flow characteristics, blood pressure (BP), pulse wave form, respiratory rate, bioimpedance, skin chemical measurements, body weight, and direct water ingestion measurement. These additional biological indicators can be used alone or in combination with the biological indicators described above in order to determine the hydration index of the individual.

The data collected from the biological sensors 104 can include data indicative of the motion of the user in additional to the biological indicators described above. For example, the wearable device can include an inertial motion unit (IMU), including accelerometer, gyroscope and magnetometer data, and localization data from, for example, a global positioning system (GPS) which can be operable to provide data to the biological sensors. The biological sensor data 104 can also include environmental data, including ambient temperature (t$_{ambient}$), altitude, ultraviolet (UV) exposure, and ambient humidity. Finally, the biological sensors 104 can be embedded, or in other examples external to, the device. Additionally, the biological sensors 104 can be communicably coupled with the wearable device through a wired or wireless interface (e.g., Bluetooth, Bluetooth Low Energy (BLE), ANT+, Zigbee, etc).

In at least one example, the method 100 can include creating the baseline data 102 by evaluating user demographic data 110. On average, users with the same demographic characteristics tend to share, with varying degrees of similarity, hydration, water loss, water absorption and hydration index characteristics. As such, relevant demographic data can include, but is not limited to, the age, gender, weight, height, body mass index, total skin area, tissue fat percentage, Fitzpatrick skin type, and genetic ethnicity of an individual. Thus, demographic data can aid in providing a more accurate overall hydration index analysis.

At block 106, the method determines whether the initial data collection period has elapsed. If the initial period has not elapsed, the method continues to collect baseline data 102. In the alternative, once the initialization period has elapsed, the collected baseline data 102 can be stored as baseline data 108 at a local or remote location for later comparison. That baseline data 108 can also be influenced by demographic data 110 pertinent to the specific user. For example, older adult users may be expected to require a higher baseline hydration level compared to younger adult users. The demographic data 110 can be obtained, for example, by having the user enter the data directly onto the device, or through wired or wireless communication, after which the demographic data 110 is entered in a web-based, or smartphone, application. It should be noted that the use of pre-established baselines based on demographic data can allow for the hydration index values to be determined and posted more quickly after device initialization. This avoids the need for having to wait for the initialization period, and can potentially increase the accuracy of the information obtained.

At block 112, the method 100 can continue to collect new, real-time biological data 112 via the biological sensors 104. At block 114, the new biological data 112 can be then filtered to emphasize the data collected during periods of rest. For example, data collected from the IMU as well as geographic data can be used to determine when periods of rest occurred. The filtering process can be completed using a mathematical analysis including one or more data pre-processing methods. For example, mathematical algorithms used can include, but are not limited to, a moving average filter, a low-pass filter implemented, such as, as a finite impulse response (FIR) filter or an infinite impulse response (IIR) filter. As used herein, the term pre-processing can include analyzing raw measurements of a biological indicator to make the data more conducive to comparison with a baseline; this can be done through methods of normalization or filtering, as described above. In at least one example, pre-processing can include removing random spikes in the data to obtain a more stable, workable baseline indicator curve. The data pre-processing can include linear and non-linear techniques for curve fitting including, for example, polynomial fits to the input data, neural networks, piecewise-linear regression functions, Bayesian filters, support vector machines, and least-square polynomial fit algorithms. The methods for data pre-processing described herein can be used individually or be run in parallel. Such methods can allow raw data collected over a period of time to be analyzed to determine and output a baseline for the given metric. For example, the pre-processing step can be used to remove noise and other corrupt data peaks from the raw data in order to retain the data specifically related to changes in hydration level. The hydration state of an individual is not a rapidly changing metric, therefore the baseline value of each biological indicator can be determined by filtering, or averaging, data collected over a period of time. Such pre-processing methods can be extremely helpful in filtering out corrupt data or noise when data is collected from multiple biological indicators for evaluation.

At block 116, the method 100 compares the pre-processed data 114 to the stored baseline data 108, calculating the differences and relative differences of multiple parameters. Next, at block 118, the method performs a non-linear operation with the combination of differences determined at block 116. The non-linear operations can range from simple lookup tables that convert the input values into previously stored values of the hydration index to more complex algorithms including, for example, neural networks, Bayesian filter, and support vector machines. The non-linear operations may also include hidden Markov models or extended Kalman filters that keep track of the hydration state of the user over time, and analytic functions can calculate the hydration index as a function of the deviation from the baseline inputs.

At block 120, the hydration index values from the non-linear operations are compared to a range of expected values based on the values stored in the baseline data 108. The range can be calculated based on the data collected during the initialization period described above. For example, when an individual is first analyzed the maxima and minima of each biological indicator may not be known. However, as data is collected the information can be used to create an upper and lower bound for the individual's biological signal, creating a range of expected values. The method 100 can then use these expected values to further analyze the newly collected data. If the value is within range, then the method 100 proceeds to block 122 and the hydration index is posted. If the value is considered substantially close to being out of range, then the method 100 proceeds to block 124 and the baseline values are adjusted to bring them into range (plus a margin). In at least one example, "substantially close" can refer to within about 25% of the previously recorded range. In an alternative example, "substantially close" can refer to within about 10% of the previously recorded range. In yet another example, "substantially close" can refer to within about 1% of the previously recorded range. The method 100 as described is constantly improving in accuracy based on the information collected. As such, as an individual continues to use a hydration tracking method in accordance with method 100, the range of expected values can adapt over time, improving the accuracy of the method.

After the hydration index values are in the range, the method 100 proceeds to block 122 and the hydration index is posted. For example, if the hydration index value is considered to be excessively high then the baseline values are adjusted to provide a lower hydration index. As such, over a period of time the algorithm can learn the true, euhydrated state of the users based on the biological indicators. The method can then be capable of periodically adjusting the baseline data values based on the range of values observed in the past up to a given point in time. Additionally, the hydration index values posted by the algorithm may become increasingly more accurate over time. It should be noted that the method 100 as described with respect to FIG. 1 is just one example of several methods which are capable of solving the initial estimate problem. As such, one having skill in the art would recognize that other methods could be used without deviating from the present disclosure.

Figure 2:
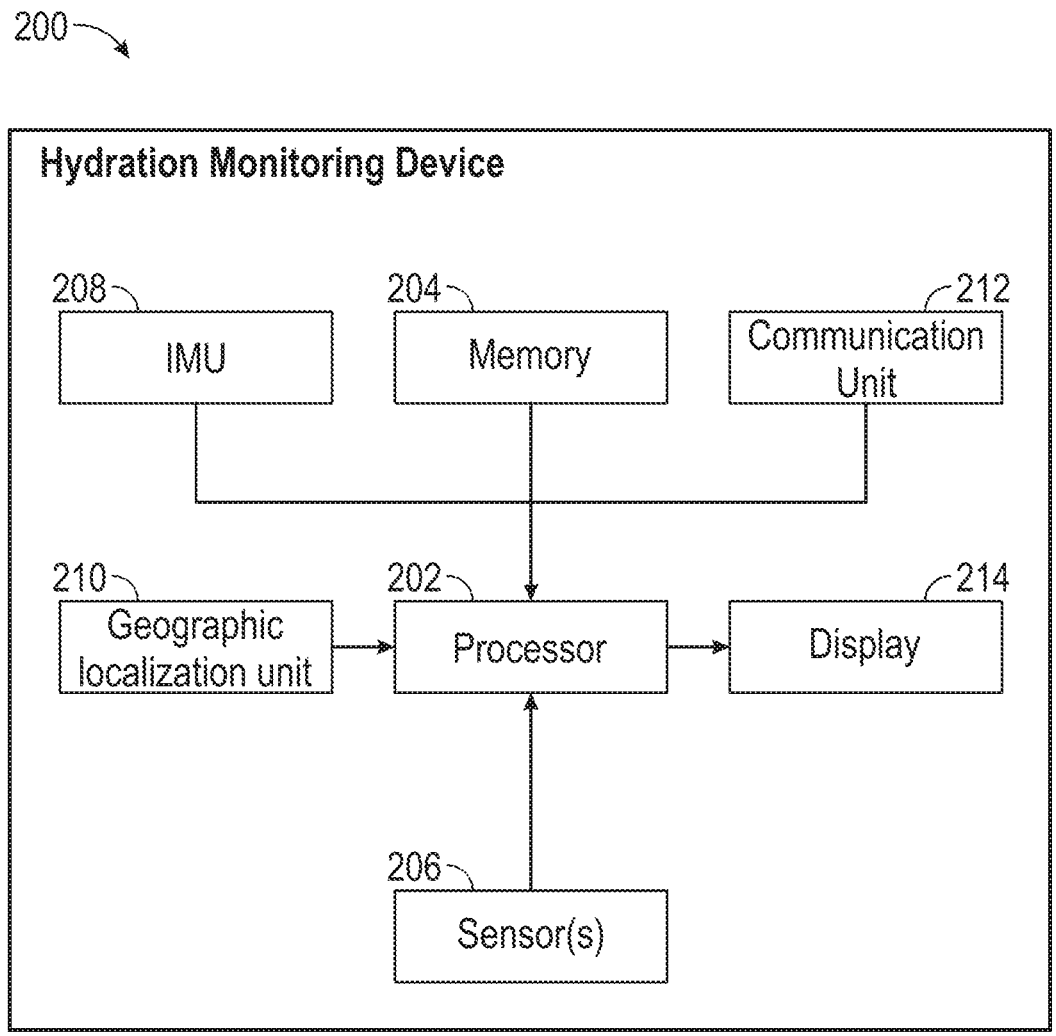
FIG. 2 illustrates components of an exemplary wearable device in accordance with the disclosure herein.

FIG. 2 illustrates an exemplary schematic diagram depicting the main components which may be included in a hydration monitoring wearable device 200 in accordance with the present disclosure. The wearable device 200 can include a processor 202 and memory 204 which enables the wearable device 200 to execute, for example, the method 100 described in FIG. 1. In at least one example, the wearable device 200 can contain one or more sensors 206 communicable with the processor 202 and operable to convey data relating to one or more biological indicators to the processor 202. In at least one alternative example, the wearable device 200 can contain an IMU 208 communicable with and operable to convey motion data to the processor 202; one or more sensors 206 communicable with and operable to convey environmental information to the processor 202; a geographic localization unit 210 communicable with and operable to convey geographic localization data to the processor 202; and a communication unit 212 operable to allow the device 200 to communicate with (through wired or wireless communication methods) a server, the user's smartphone, or personal computer (PC). Finally, the wearable device 200 can also contain a display 214 operable to allow the processor to display, among other information, a calculated hydration index. While FIG. 2 generally depicts the hydration-monitoring device as a wearable device, it should be understood by those of skill in the art that the hydration-monitoring device could be a non-wearable device without departing from the spirit of the present disclosure.

Figure 3:
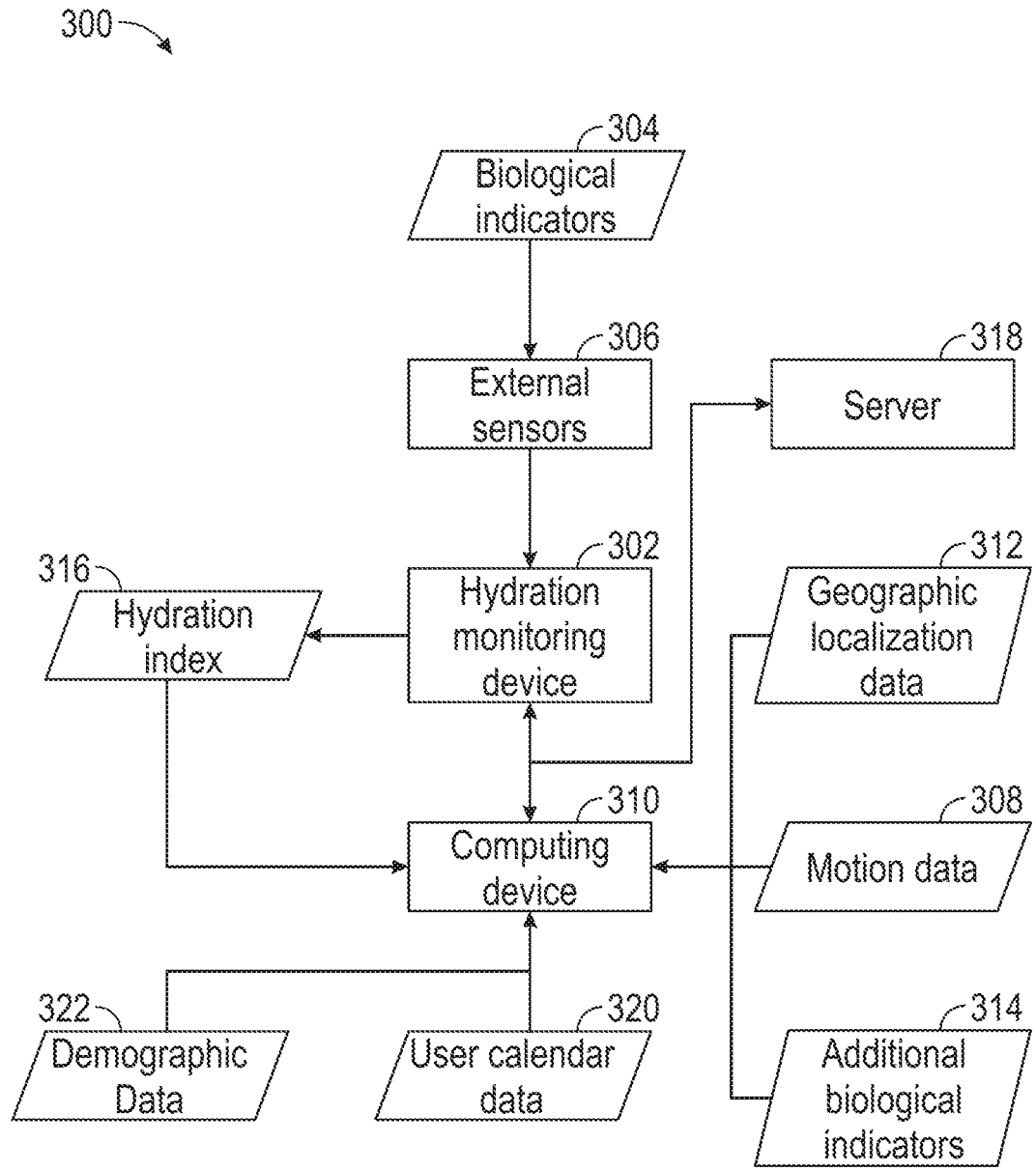
FIG. 3 illustrates a schematic diagram of the hydration monitoring system in accordance with the disclosure herein.

FIG. 3 depicts a schematic diagram of a hydration monitoring system 300 in accordance with the disclosure herein. The hydration monitoring system 300 can include a hydration monitoring device 302, operable to receive data relating to biological indicators 304 from one or more external sensors 306. In at least one example, the data received from the one or more external sensors 306 can be combined with the biological data that the hydration monitoring device 302 captures itself via internal sensors. In at least one example, the external sensors 306 can include, but are not limited to, wireless scales, drink monitoring devices (such as the H2OPal or MyHydrate), glucose measurement devices, total hemoglobin measurement devices, $SpO_2$ monitors, and the like. The hydration monitoring device 302 can also receive user motion data 308 from an IMU and sensors embedded in a computing device 310. The hydration monitoring device 302 can communicate with the computing device 310, for example by using the wireless communication protocols described above. The computing device 310 can also be operable to provide the hydration monitoring device 302 with geographic information 312 (via GPS, cellular data, or WiFi, for example), motion data 308, and/or additional biological indicators 314. User demographic data 322 can additionally be made available to the hydration monitoring device 302 via the computing device 310, as described in detail above. The computing device 310 can be a smartphone, a wearable electronic device, a personal computer (PC), or other handheld electronic device. Furthermore, the user's calendar 320 can be made available through the same means. The user's calendar 320 can provide the hydration monitoring device 302 with information concerning the user geographic location and physical activity.

The hydration monitoring device 302 can be operable to generate and post the user's hydration index 316 using methods described above, which can then be displayed directly on the hydration monitoring device 302 using an embedded display. The hydration index 316 may also be supplied back to the computing device 310 via computer or smartphone applications. The computing device 310 can also be operable to store the hydration index 316, along with other pertinent user information, to a cloud-based server 318. Storing the information on a server can allow for centralized aggregation of data from multiple users, facilitating the mining of user data and the future improvement of the hydration monitoring algorithm described in detail below.

In addition to the hydration monitoring methods described above, volume loss models can also be used in order to increase the accuracy of the hydration monitoring device described herein. Specifically, most users tend to have a small baseline loss; however significant losses can occur throughout the day due to sweating. Such losses can be tracked in real-time using the hydration monitoring device, and the information can be used to anticipate how the loss will affect the overall hydration of the user. Including anticipatory loss information can increase the accuracy of the hydration monitoring system described herein.

An additional element which can be considered in the present hydration monitoring evaluation is the intake of fluids. To provide the most accurate information, a user's fluid consumption must be taken into account. Such events can be monitored, for example, through the use of gesture/motion data received by the smartphone, as described with respect to FIG. 3. Additionally, swallowing can have a small, but recognizable effect on cardiovascular and respiratory systems, which can be monitored by the biological sensors described above. The hydration monitoring system described herein can be operable to monitor not only hydration loss, but also rehydration by a user, such that the hydration monitoring device is capable of providing the most accurate real-time information possible.

The following examples are provided to illustrate the subject matter of the present disclosure, including methods for tracking a hydration level of an individual. These examples are not intended to limit the scope of the present disclosure, and should not be so interpreted.

Example 1

In the present example, a combination of several biological indicators were monitored including, but not limited to, heart rate (HR), NIRS fractional water (pH2O), and skin temperature ($T_{skin}$). Data was captured from 12 unique subjects, after written informed consent, over a period of 36 trials in which each subject consumed different volumes of fluids ranging from zero to 8.4 mL per kg of nude body weight (NBW). The resting biological indicator data was captured for a period of 12 minutes at two points in time, the first measurement was taken immediately before fluid consumption and the second measurement was taken approximately 42 minutes after the fluid had been ingested, allowing one to measure differential values of each subject under different levels of hydration. The change in the value of the combination of multiple biological indicators can be represented by Equation 1.

$$\Delta\%M = 100(M_{present} - M_{previous})/M_{previous} \quad (1)$$

wherein $\Delta\%$ M is the percent difference of a given metric (M), between the present value ($M_{present}$) and the previously measured value ($M_{previous}$), before volume ingestion. For example, the change in percent of resting heart rate (RHR) can be determined as follows, $\Delta\%$ RHR=100(RHR$_{present}$-RHR$_{previous}$)/RHR$_{previous}$.

For the purposes of the present example, a multivariable regression model was built using the data available from the trials monitoring the change in three biological parameters. In the present example, the p-value associated with the multivariable regression model is p<0.05. The multivariable regression model for determining ingested volume $V_{in}$ described herein can be represented by Equation 2.

$$V_{in} = NBW_e(8.77 - 0.263\Delta\%RHR + 0.0765\Delta\% RpH2O + 0.614\Delta\%RT_{skin} + 0.0267\Delta\%RHR^2 - 0.00662\Delta\%RHR\Delta\%RpH2O + 0.0177\Delta\%RpH2O\Delta\%RT_{skin}) \quad (2)$$

where $NBW_e$ is the current estimate of the euhydrated nude body weight of the user, RHR is resting heart rate, RpH2O is the resting pH2O coefficient, and $RT_{skin}$ is the skin temperature at rest (measured in degrees centigrade).

In the above example, the three biological indicators RHR, RpH2O and $RT_{skin}$ were chosen as preferred biological indicators for evaluating the hydration level of a user. Other possible biological indicators, such as resting total hemoglobin concentration (tHb) and resting tissue oxygenation (SmO2), were not selected because the p-values, provided by an Analysis of Variances (ANOVA), presented a higher probability of the null-hypothesis that their explanation of the variation of the ingested volume was purely random. The same p-value based selection process was performed in the selection of the second order and cross-terms included in the regression model. The p-value associated with each biological parameter of the multivariable regression analysis of Eqn. 2 is indicated in Table 2.

TABLE 2

| Term | p-value |
|---|---|
| Constant | 0.001 |
| $\Delta\%$ RHR | 0.208 |
| $\Delta\%$ pH2O | 0.034 |
| $\Delta\%$ $RT_{skin}$ | 0.346 |
| $\Delta\%$ $RHR^2$ | 0.062 |
| $\Delta\%$ RHR $\Delta\%$ pH2O | 0.062 |
| $\Delta\%$ RpH2O $\Delta\%$ $RT_{skin}$ | 0.136 |

Figure 4A:
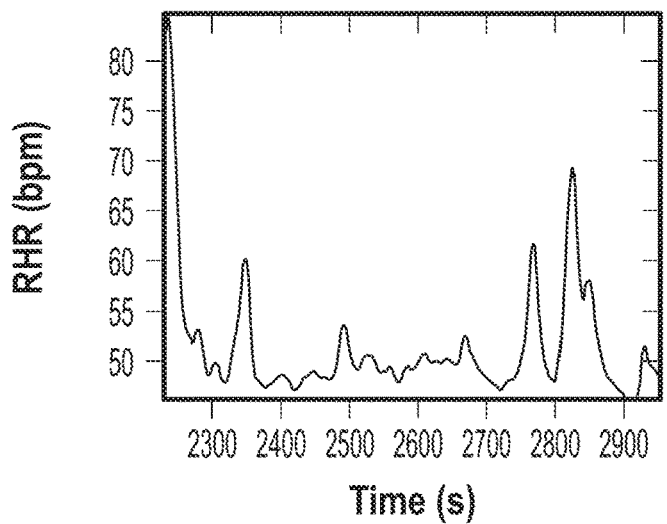
FIG. 4A is a graph illustrating the resting heart rate of a user without fluid ingestion.
Figure 4B:
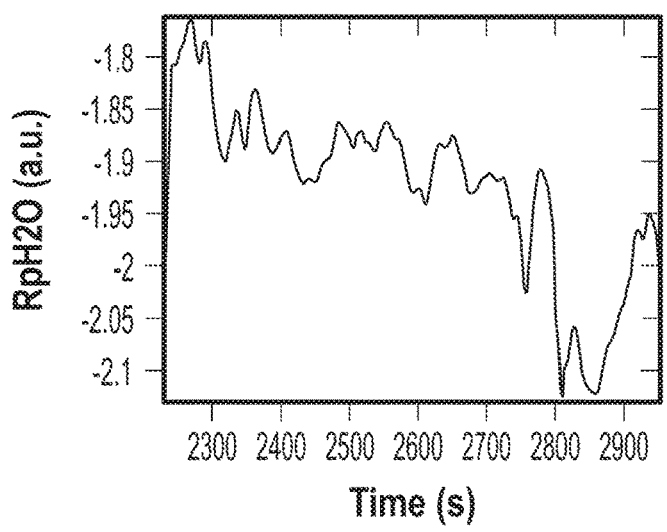
FIG. 4B is a graph illustrating the resting near-infrared spectrometer fractional water coefficient signal of a user without fluid ingestion.
Figure 4C:
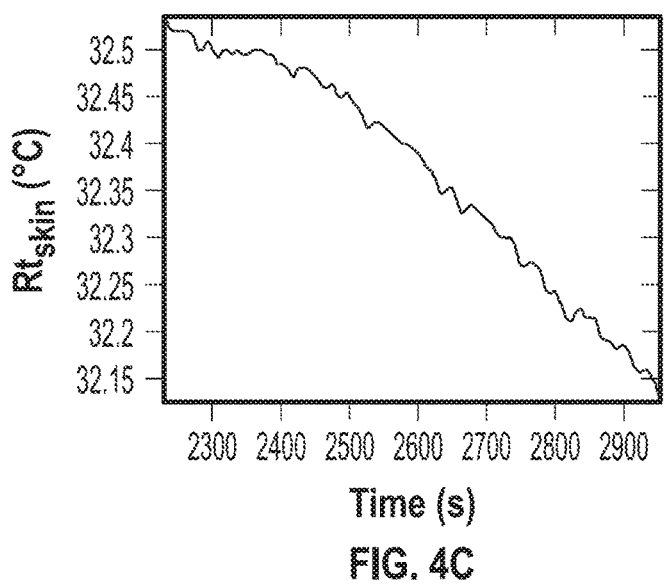
FIG. 4C is a graph illustrating the resting skin temperature of a user without fluid ingestion.

The following is an example of how to use Equation 2 and the resting values of the selected biological indicators to estimate the volume of fluid ingested by a user. This example uses actual data from one of the trials from a subject (a 19-year-old female) who participated in the study. The plots shown in FIGS. 4A-4C show examples of the resting HR, pH2O, and $T_{skin}$ data captured prior to fluid ingestion, respectively. Specifically, during this period of time, the subjects were not ingesting any fluid, and thus were becoming dehydrated (moving away from their individual baseline, euhydrated states). The plotted data was pre-processed by applying a 12-second moving-average filter. For the resting value of each metric, 2% trimmed mean (i.e., the mean excluding the 2% highest and lowest values) was calculated, thus removing outliers. This resulted in initial values for RHR, RpH2O and $RT_{skin}$, 50.899 bpm, −1.923 and 31.947° C., respectively, where RpH2O is the resting pH2O coefficient and $RT_{skin}$ is the resting skin temperature.

Figure 5:
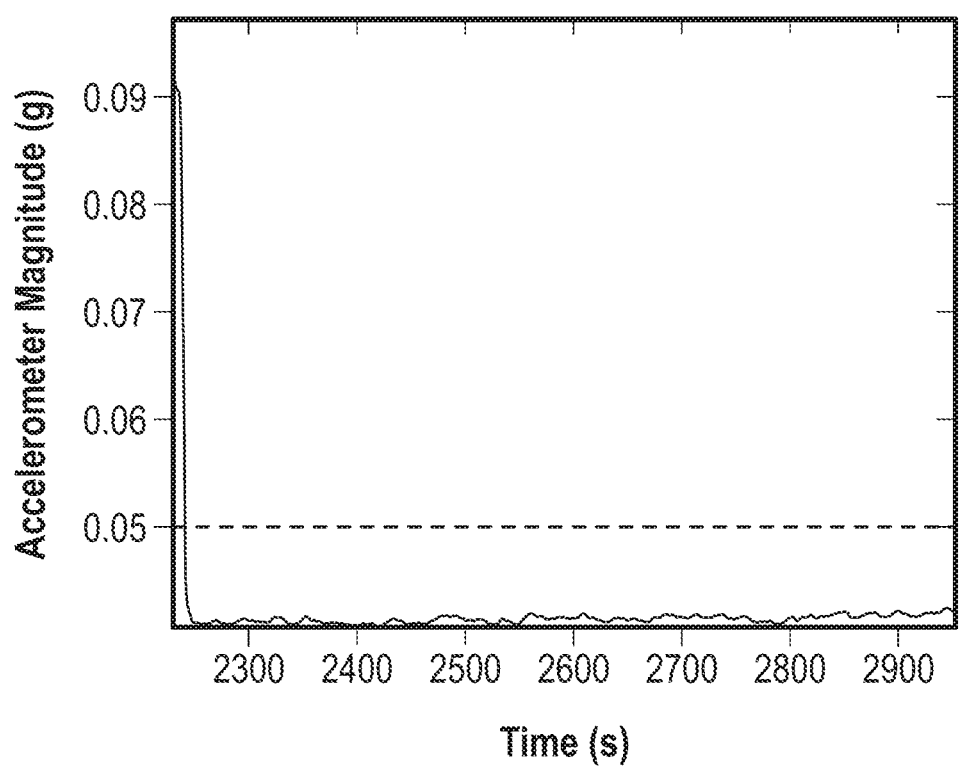
FIG. 5 is a graph illustrating the magnitude of the accelerometer signal with gravity removed.

The subject was sitting down before the rest period. Then she moved from a chair to a cot where she lied down during the resting period. FIG. 4A indicates the resting heart rate of the subject for a period of time prior to volume ingestion of fluids. The change in posture gives rise to the spike in heart rate seen right at the beginning of the RHR plot shown in FIG. 4A. The presence of motion can be confirmed by looking at the plot shown in FIG. 5, which shows the magnitude of the accelerometer, with the acceleration of gravity removed, after a 12-second moving-average filter. This plot in FIG. 5 is 10 seconds earlier than the resting plots shown in FIGS. 4A-4C, thus being able to show more clearly the peak in movement that takes place right before the subject lies down. In FIG. 5, the dashed line indicates the threshold value for movement detection. FIG. 5 is also an example of how an IMU signal can be used to detect rest periods: setting the magnitude threshold of the 12-second averaged accelerometer signal after processing to remove gravity at a value of, for example, 0.05 g (dashed line), allows one to make sure that the user has been substantially at rest for at least the duration of the moving-average filter by selecting periods of time when the time-averaged accelerometer signal is below the selected threshold.

Figure 6A:
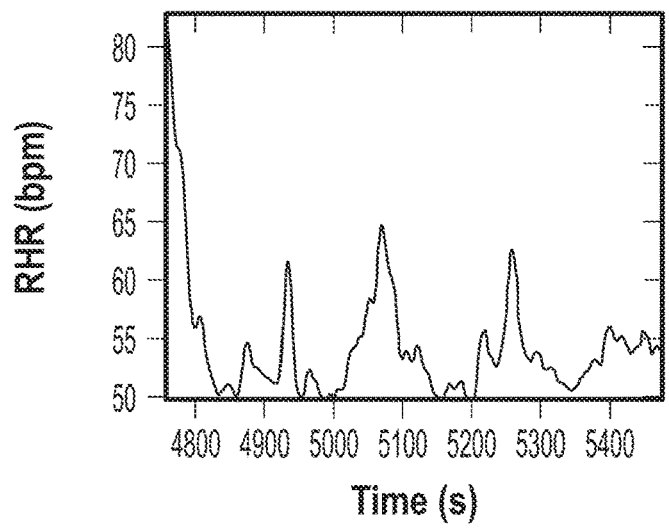
FIG. 6A is a graph illustrating the resting heart rate after fluid ingestion.
Figure 6B:
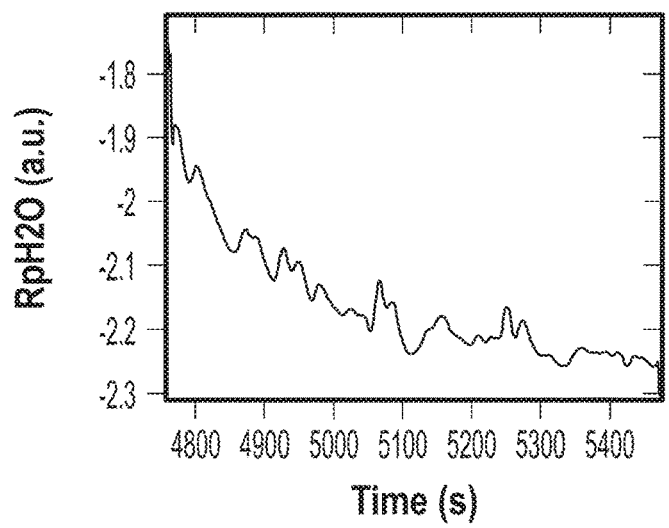
FIG. 6B is a graph illustrating the resting near-infrared spectrometer fractional water coefficient signal of a user after fluid ingestion.
Figure 6C:
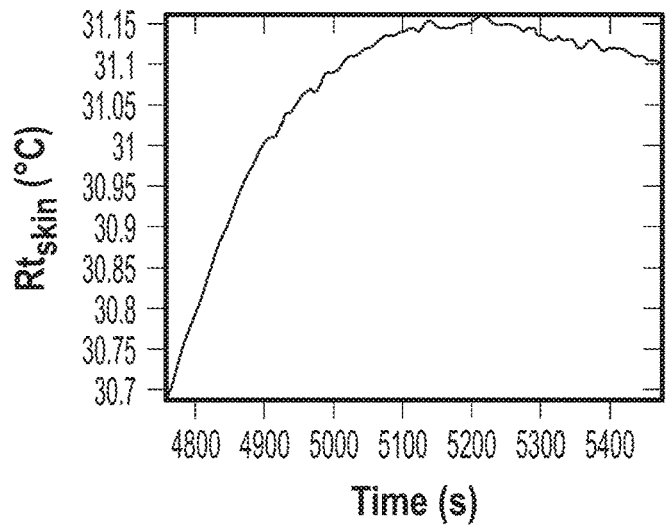
FIG. 6C is a graph illustrating the resting skin temperature of a user after fluid ingestion.

The plots shown in FIGS. 6A-6C depict the resting HR, pH2O, and $t_{skin}$ signals captured 42 minutes after ingestion of 466 mL of an electrolyte solution. After 42 minutes, the fluid had enough time to be digested and absorbed into the subject's blood stream. The trimmed mean values at this point in time are 54.095 bpm, −2.1628, and 31.947° C., for RHR, RpH2O and $RT_{skin}$, respectively.

Hence, for this example Δ% RHR=6.280, Δ% RpH2O=12.49 and Δ% $RT_{skin}$=−2.146. In the present example, the subject has a nude body weight of 68.3 kg (NBW=68.3 kg). Applying the above values to Equation 2 as defined above, $V_{in}$=466 mL. Compared to the actual volume consumed of 478 mL that corresponds to a residual error ($V_{in}-V_{actual}$, or volume ingested minus actual volume) of −12 mL, or only −0.41 oz.

It should be noted that the $V_{in}$ value can be negative, effectively meaning that the same equation can be used to detect both fluid volume gains and losses. It should also be noted that the value calculated by the multivariable regression model is not restricted to being a physical volume (such as, mL or oz) but can be instead an index that is proportional, or a function of, a physical volume. In some examples, the index can also be unitless or expressed in terms of arbitrary units.

Example 2

Figure 7A:
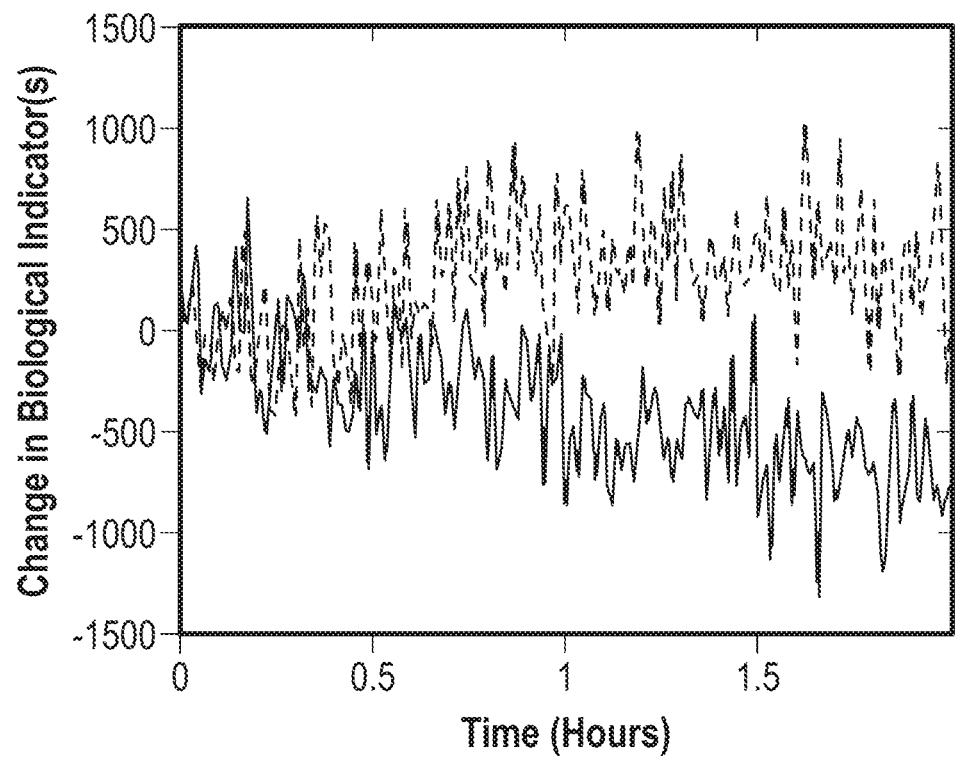
FIGS. 7A and 7B illustrate a comparison of the change in a combination of multiple biological indicators between an actively hydrating group and a control group.
Figure 7B:
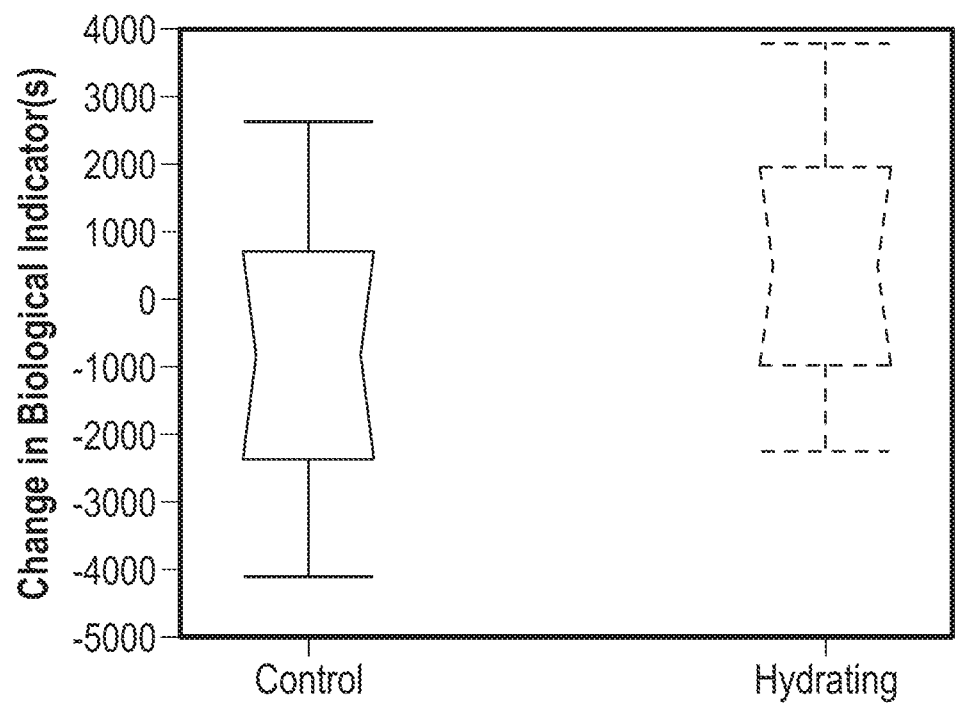

In the present example, a portion of the subjects were hydrated ("hydrating group"), and the rest of the subjects were not provided any means of hydration ("control group"). All subjects in the present example were then observed while performing predetermined tasks for a time of roughly 1.5 hours. The ingestion of the fluids for the portion of the subjects that were provided with hydration was spaced out in order to maximize the absorption of the fluids. During the experiment, a combination of one or more biological indicators were measured, such as skin perfusion and tissue oxygenation indicators, the results of this example are indicated in FIGS. 7A-7B.

In this example, both the hydrating group and the control group began the experiment at a euhydrated state. The differences in deviation from baseline hydration (euhydrated state) with respect to a combination of one or more biological indicators (such as, total hemoglobin content (tHb) and tissue oxygenation (SmO2)) was monitored in both groups and is illustrated on the graph in FIG. 7A. Specifically, the dotted line represents the change in hydration of the hydrating group, while the solid line reflects the change in hydration of the control group. The data provided in FIG. 7A indicates that as the subjects performed their tasks, the control group showed a greater change in the biological indicators monitored, steadily moving from a euhydrated state to a dehydrated state, while the hydrating group maintained a lower change in biological indicators. FIG. 7B indicates that the hydrating group as a whole maintained a higher hydration level than the control group.

The data collected from the hydrating group and the control group was then used to build estimates of hydration index by applying mathematical algorithms, such as those described above. Once the data is evaluated it can be determined whether the hydration strategy applied to the hydrated group was successful in maintaining a desired hydration level; such information can assist in determining long-term hydration trends within a specific subject.

Example 3

Resting periods of subjects were studied throughout the day in order to analyze the change in hydration status over an extended period of time and the impact of hydration on one or more biological indicators. For the purposes of this example, resting heart rate (RHR) is monitored, however any of the biological indicators describe above could be monitored using similar methods as described herein. In this example, the baseline RHR of the subjects was obtained from overnight data, and served as a reference RHR to compare against the RHR from various resting periods throughout the next day. For each day, the changing resting heart rate Δ% RHR was determined using Equation 3.

$$\Delta\%RHR=(RHR_0-RHR_{t_1})-(RHR_0-RHR_{t_n})/RHR_0 \quad (3)$$

where $RHR_0$ is the baseline resting heart rate, $RHR_{t_1}$ is the resting heart rate at the beginning of the duration of measurement, and $RHR_{t_n}$ is the resting heart rate at the end of the duration of measurement.

In this study, two sub-experiments were performed in order to determine whether changes in hydration status affected the resting heart rate and whether resting heart rate can be used as an indicator of hydration status.

Figure 8A:
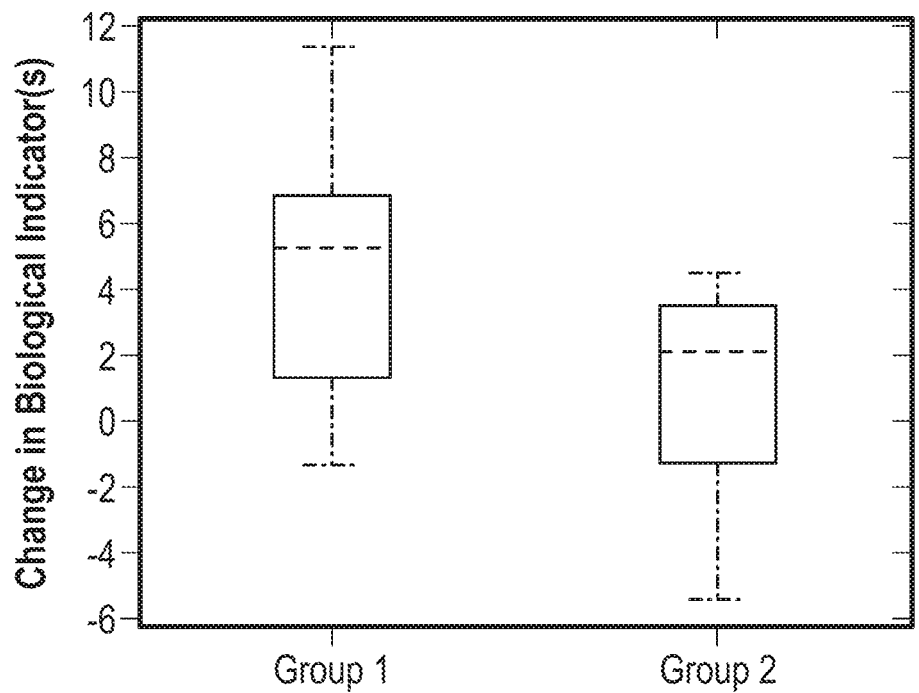
FIGS. 8A and 8B are graphs indicating the effect of hydration on a single biological indicator.

In the first sub-experiment, the subjects were split into two groups. RHR data was collected from each of the two Groups over a period of two days, still periods of time of longer than 15 minutes was used to obtain a baseline RHR for each subject. Group 1 was allowed to consume fluids throughout the day, followed by a day of not drinking any fluids, or vice versa. While Group 2 was not allowed to consume fluids. Throughout each day of observation, the subjects engaged in various activities including napping, sitting, walking, exercise, and a period of time in a sauna. The percentage change in RHR between the start of the measurement duration ($t_1$) and the end of the measurement duration ($t_n$) were taken as data points. FIG. 8A illustrates a graph showing the results of both Group 1 and Group 2 during the first sub-experiment. All data points from Group 1 are grouped together and all data points from Group 2 grouped together to provide a graphical analysis of the effects of hydration. As indicated in FIG. 8A, Group 2, which was not allowed to consume fluids, showed a more significant change in heart rate ($\Delta\%$ RHR) at the end of the measurement duration ($t_n$).

Figure 8B:
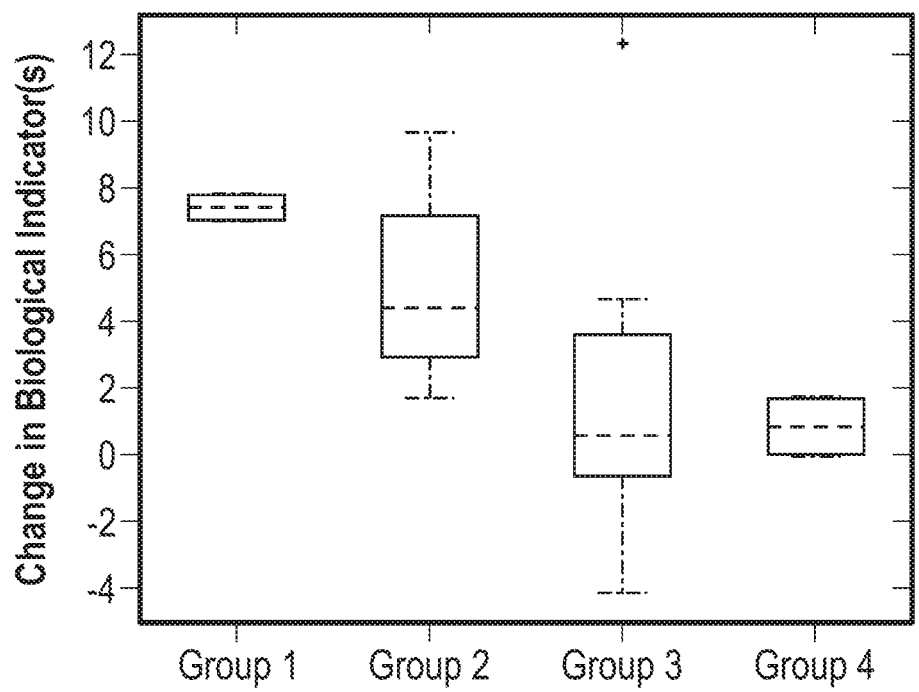

The second sub-experiment allowed the subjects to consume varying amounts of water throughout the day. The subjects were divided into four groups, Group 1 consumed no water, Group 2 consumed a small amount of water (less than 400 mL), Group 3 consumed a larger amount of water (between 400-900 mL), and Group 4 consumed the largest amount of water (over 900 mL). Again, data was collected over a two-day period, and still periods of greater than 15 minutes was used to create a baseline resting heart rate. As with the first sub-experiment, the subjects engaged in activities including napping, sitting, walking, exercise, and a period of time in a sauna, and the percentage change in RHR between the start of the measurement duration ($t_1$) and the end of the measurement duration ($t_n$) were taken as data points. FIG. 8B illustrates the effect of water consumption on resting heart rate for varying amounts of water consumed. The change in biological indicators with respect to the baseline hydration level can be used to determine the hydration index of the individuals. As shown, the median $\Delta\%$ RHR for Group 1, which did not consume water, was greater than the median $\Delta\%$ RHR than the Groups that were allowed to consume varying amounts of water. For Groups 2-4, where subjects drank varying amounts of water, the volume of water consumed had a clear effect on RHR throughout the day. Group 4 consumed the largest amount of water and showed the least variation in RHR. Specifically, as shown, Group 1 has had a significant change from the baseline and is thus likely dehydrated. However, Group 4 has had relatively no change, and is considered hydrated, or even hyper-hydrated.

Example 4

Figure 9A:
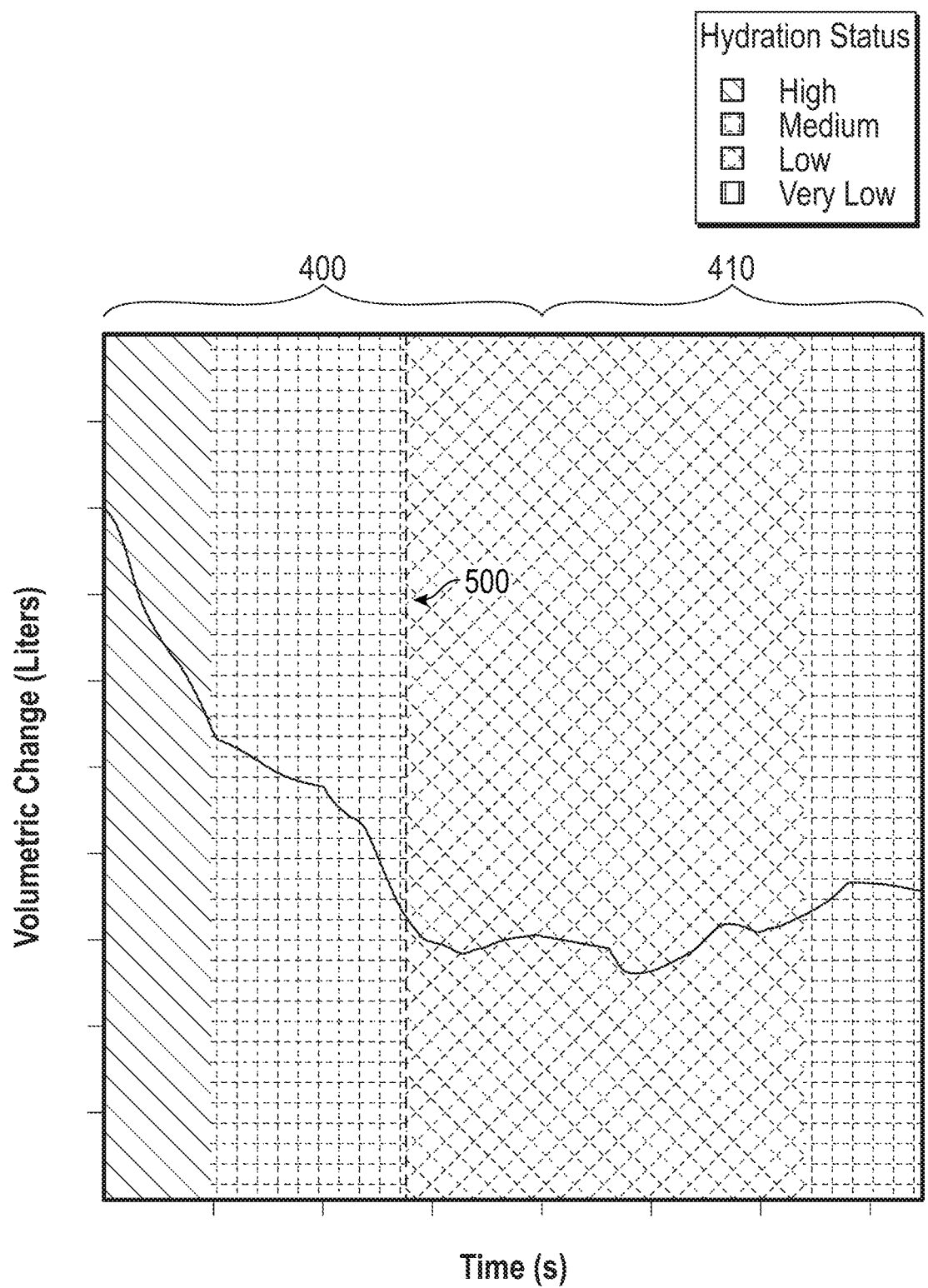
FIGS. 9A-9K are graphs indicating the effect of hydration on a combination of one or more biological indicators.
Figure 9B:
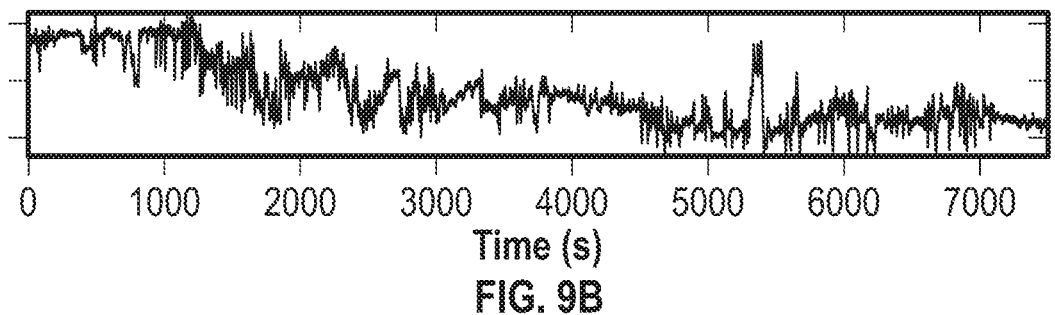
Figure 9C:
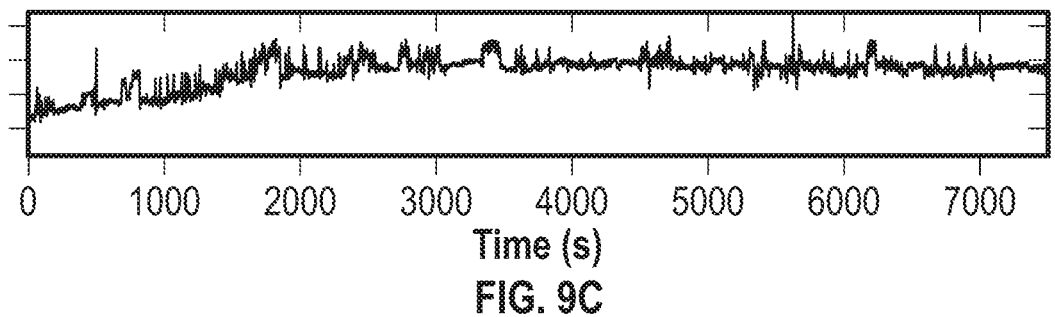
Figure 9D:
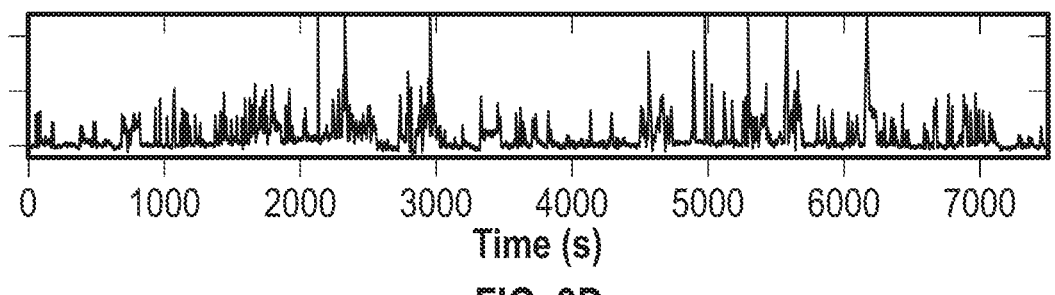
Figure 9E:
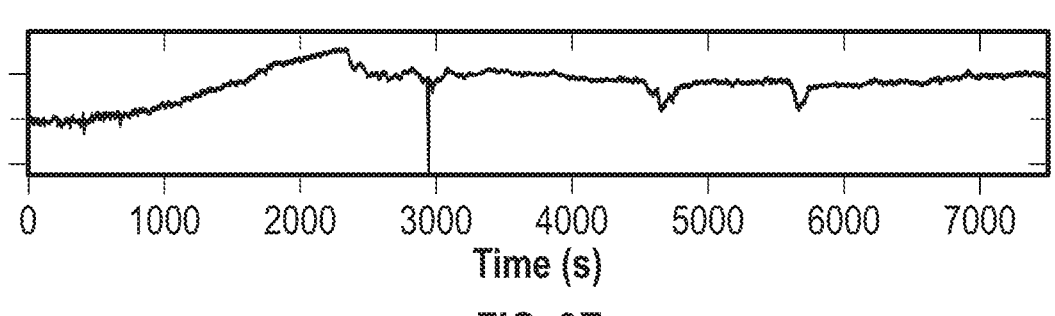
Figure 9F:
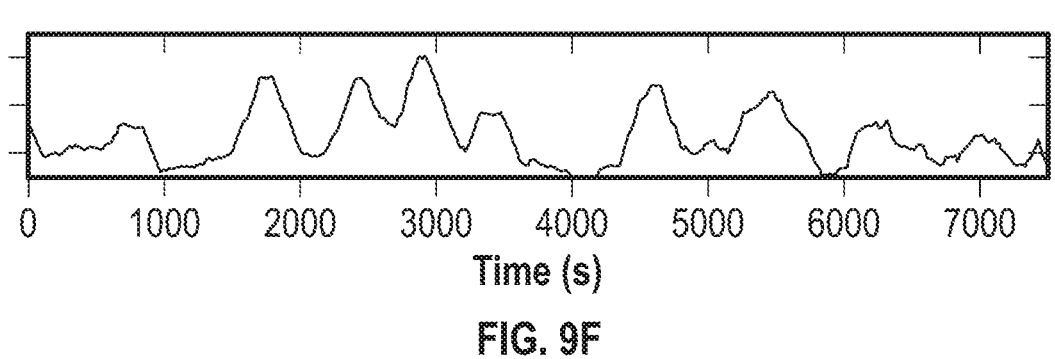

In this example, the effect of hydration is monitored with respect to multiple biological indicators including NIRS fractional water (pH2O), skin perfusion (stHb), tissue oxygenation (SmO2), and total hemoglobin concentration (tHb). FIG. 9A indicates the hydration status of a subject during continuous exercise. For the purposes of this example, first period of exercise 400 is quantified as hard exercise, while the second period of exercise 410 is quantified as moderate exercise. As indicated in the graph illustrated in FIG. 9A, the volumetric change in hydration decreases as exercise continues. The subject is allowed to consume water after a period of time indicated by vertical line 500, after which the hydration state of the subject slowly increases. Various biological indicators were monitored during this experiment and changes in such biological indicator are shown in FIGS. 9B-9F. For example, the graph in FIG. 9B indicates a change in pH2O over time, the graph in FIG. 9C indicates a change in skin perfusion over time, and the graphs in FIGS. 9D-9F indicate various readings received from one or more external sensors with respect to time.

Figure 9G:
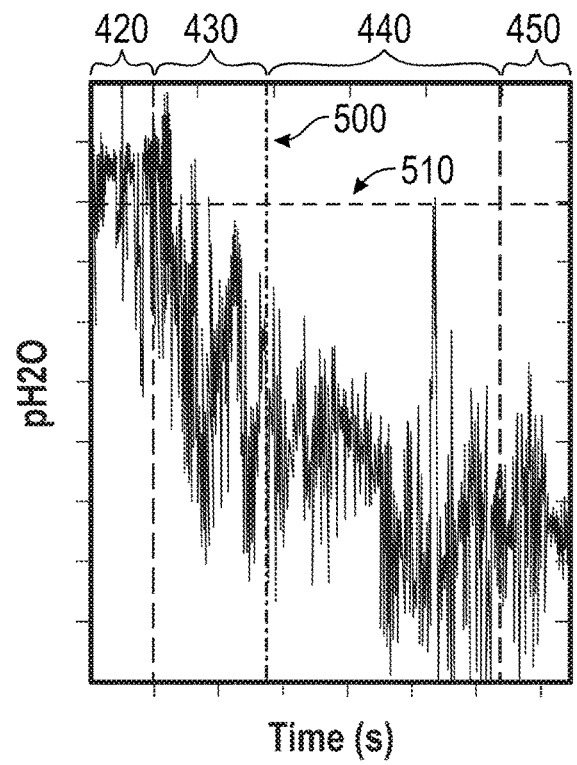
Figure 9H:
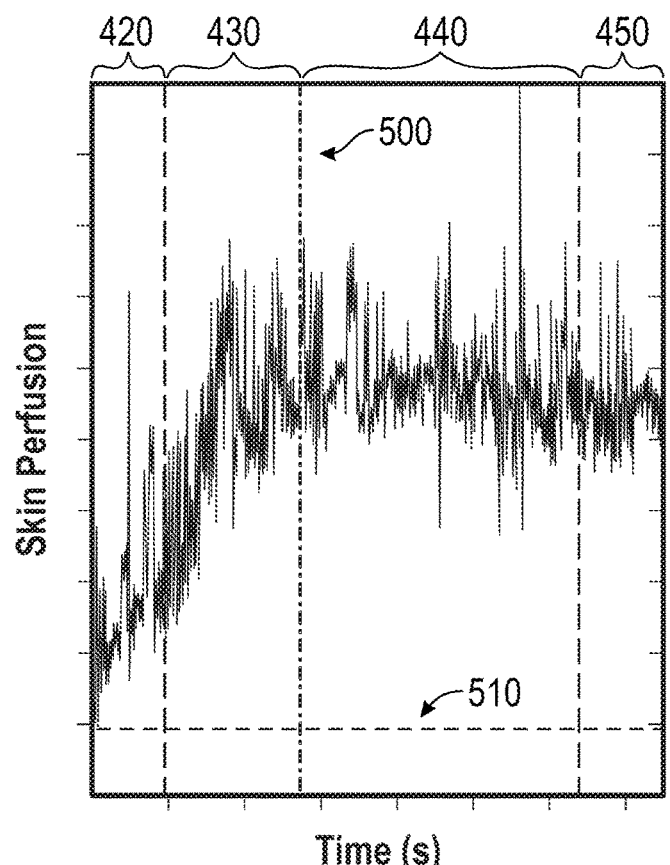
Figure 9I:
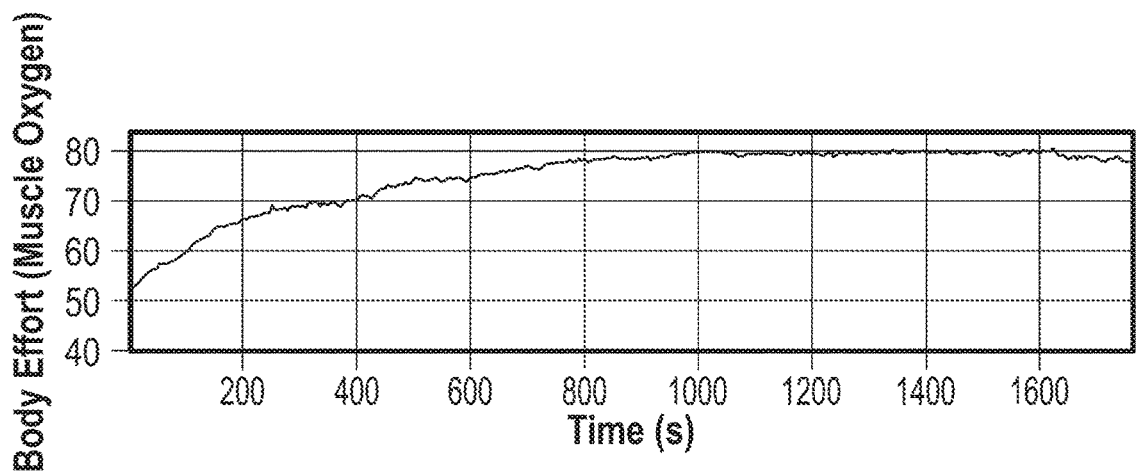
Figure 9J:
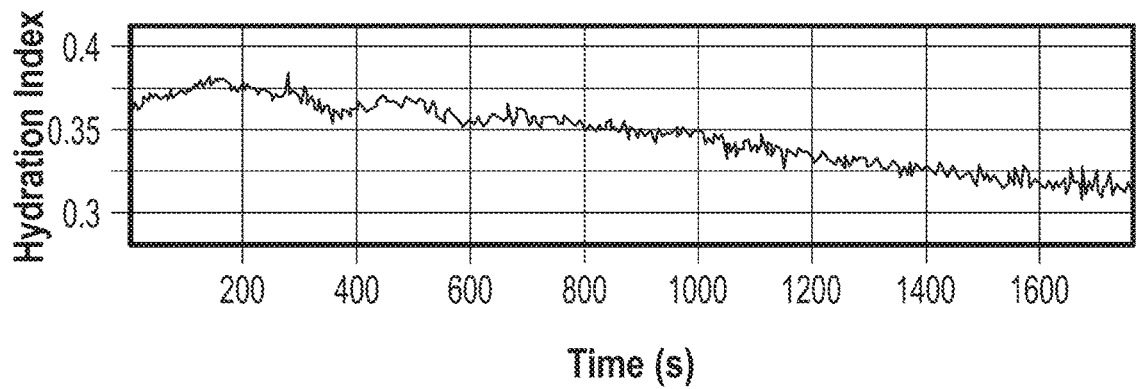
Figure 9K:
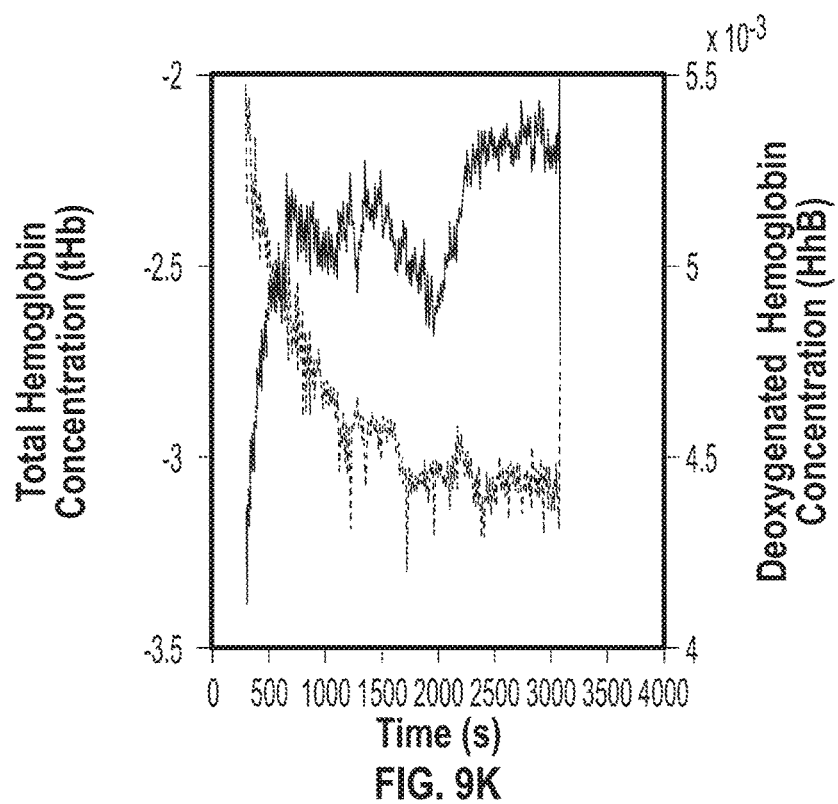

FIGS. 9G-9K are enlarged graphs showing the effect of hydration on various individual biological indicators based on the data presented in FIG. 9A. The baseline level for the individuals is represented on the graph as line 510. FIGS. 9G and 9H represent the change in NIRS fractional water level and skin perfusion over a period of time. Each of FIGS. 9C and 9D includes a period of high hydration 420, followed by a period of moderate hydration 430. During the period of moderate hydration 430, the individual consumed a predetermined amount of fluid at a predetermined time represented by vertical line 500. The period of moderate hydration 430 is followed by a period of low hydration 440. The period of low hydration is then followed by a second period of moderate hydration 450, as the fluids consumed earlier begin to affect the hydration level of the individuals. The NIRS fractional water level change corresponding to the adjustment of hydration level shown in FIG. 9A is shown in FIG. 9G. As indicated, NIRS fractional water level decreases drastically as the subject becomes dehydrated, but begins to rise along with the hydration of the subject after water is consumed. FIG. 9H illustrates the change in skin perfusion during the hydration changes of FIG. 9A. As shown, skin perfusion increases drastically as the subject becomes dehydrated then steadies after the subject consumes water. FIGS. 9I and 9J indicate the change in tissue oxygenation (or muscle oxygenation) as it corresponds to hydration index. As shown, the muscle oxygenation level increases as the hydration index of the subject decreases. Finally, FIG. 9K indicates that hydration has opposite effects on total hemoglobin concentration (tHb), represented in a dashed line, and deoxygenated hemoglobin concentration (Hhb), represented in a solid line. Deoxygenated hemoglobin concentration reflects the amount of hemoglobin in the body without the bound oxygen, as such total hemoglobin concentration can be defined as tHb=Hhb+HbO2. As shown, the deoxygenated hemoglobin concertation (Hhb) increases with dehydration and total hemoglobin concentration (tHb) decreases.

As indicated by FIGS. 9A-9K, hydration level can have vastly different effects on different biological parameters. Thus, in order to achieve the most accurate calculation of hydration index, multiple biological indicators can be monitored and analyzed.

While the above embodiments have been described in detail in the foregoing description, the same is to be considered as illustrative and not restrictive in character, it being understood that only some embodiments have been described and that all changes and modifications that come within the spirit of the embodiments are desired to be protected.

The invention claimed is:

1. A method of monitoring hydration comprising:
determining, based on data for a user, a baseline value for the user representing a euhydrated state for the user;
obtaining, via one or more biological sensors for a wearable device, real-time biological data for the user;
filtering the real-time biological data into real-time biological data corresponding to a rest period;
determining a hydration index for the user by comparing the real-time biological data corresponding to the rest period with the baseline value representing a euhydrated state;
determining whether the hydration index for the user falls within a predetermined range of expected values; and
generating an updated baseline value based on the hydration index and demographic data corresponding exclusively to the user.

2. The method of claim 1, wherein filtering the real-time biological data is filtered using a pre-processing analysis which includes a mathematical analysis selected from the group comprising neural networks, support vector machines, Bayesian methods, linear regression methods, moving average, trimmed mean, FIR filter, IIR filter, low-pass filter, analytic function(s), extended Kalman filter, piecewise-linear regression functions, and combinations thereof.

3. The method of claim 1, wherein the baseline value is based on the data for the user over a given period of time.

4. The method of claim 1, further comprising:
   tracking a loss in fluid volume of a user based on volume loss models;
   and calculating the effect of the loss in fluid volume on the user's hydration index.

5. The method of claim 1, further comprising evaluating one or more environmental signals selected from the group comprising an ambient temperature, an ambient humidity, an altitude, an ultraviolet (UV) exposure, and combinations thereof.

6. The method of claim 1, wherein the demographic data is selected from the group comprising an age, a gender, a body mass index, a fractional fat, a weight, a genetic ethnicity, a total skin area, a Fitzpatrick skin type, and combinations thereof.

* * * * *